United States Patent [19]

Babb et al.

[11] Patent Number: 4,468,467
[45] Date of Patent: Aug. 28, 1984

[54] DIAZONIUM SALT FOR BILIRUBIN ASSAY

[75] Inventors: Bruce E. Babb, Rochester; Glen M. Dappen, Webster, both of N.Y.

[73] Assignee: Eastman Kodak Company, Rochester, N.Y.

[21] Appl. No.: 344,433

[22] Filed: Feb. 1, 1982

[51] Int. Cl.$^3$ .................... C07C 113/00; G01N 33/72
[52] U.S. Cl. ...................... 436/97; 260/141; 422/56; 436/903
[58] Field of Search .......... 436/97, 903, 164; 422/56, 57; 260/141 R, 142, 141 S

[56] References Cited

U.S. PATENT DOCUMENTS

| 2,694,720 | 11/1954 | Denton et al. | 260/141 R X |
|---|---|---|---|
| 3,511,607 | 5/1970 | Green . | |
| 3,814,586 | 6/1974 | Fraser et al. . | |
| 3,853,466 | 12/1974 | Rittersdorf et al. | 436/903 X |
| 3,923,780 | 12/1975 | Harmon et al. | 260/141 R X |
| 3,992,158 | 11/1976 | Przbylowicz et al. . | |
| 4,258,001 | 3/1981 | Pierce et al. . | |

FOREIGN PATENT DOCUMENTS 910541  12/1951  Fed. Rep. of Germany .

OTHER PUBLICATIONS

Dappen et al., Clin. Chem. 29/1, 37-41 (1983).
Griffiths et al., Chemical Abstracts, vol. 89, 1978, No. 89:76243q.
Isac et al., Chemical Abstracts, vol. 94, 1981, No. 94:174026u.
Isac et al., Chemical Abstracts, vol. 95, 1981, No. 95:61214f.
Chin-Chung Chen et al., "Sulfanilamide for the Determination of Total Bilirubin", Clin. Chem., vol. 26, No. 7, p. 990, 1980.

Primary Examiner—Arnold Turk
Attorney, Agent, or Firm—J. Lanny Tucker

[57] ABSTRACT

Diazonium salts which are useful in an assay for bilirubin are disclosed. The novel salts have the structural formula:

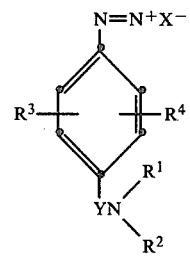

wherein $X^-$ is a stabilizing anion, Y is CO— or $SO_2$—; and $R^1$ and $R^2$ are independently selected from hydrogen, alkyl, aryl, carboxyalkyl and hydroxyalkyl providing $R^1$ and $R^2$ are not both hydrogen; $R^3$ and $R^4$ are independently selected from groups such that the sum of the Hammett sigma values for $R^3$ and $R^4$ does not exceed +0.4 or $R^3$ and $R^4$ represent the carbon atoms necessary to complete a fused carbocyclic ring structure. Reagent compositions, analytical elements and methods which use the described diazonium salt are also disclosed.

17 Claims, No Drawings

DIAZONIUM SALT FOR BILIRUBIN ASSAY

FIELD OF THE INVENTION

The present invention relates to the diazo method for the quantitative determination of bilirubin. New diazonium salts which provide sensitive and accurate assays for bilirubin are used.

DESCRIPTION RELATIVE TO THE PRIOR ART

Bilirubin is a degradation product of hemoglobin. Approximately 200 to 230 mg of bilirubin and its derivatives are formed each day in the normal human adult. As part of normal human metabolic processes, the major portion of this daily bilirubin production is excreted or degraded into other derivatives.

Excessive amounts of bilirubin occur within the human body through overproduction of bilirubin as in the case of excessive hemolysis or by retention of bilirubin due, for example, to liver failure. The result of excessive bilirubin within the human body is jaundice. Jaundice is characterized by markedly elevated serum bilirubin levels, for example, 10 mg of bilirubin per dL of serum or higher compared with the normal adult range of 0.1 to about 1 mg of bilirubin per dL of serum. There is increasing evidence that excessive amounts of bilirubin in the blood leads to an undesirable increase in bilirubin concentration within body cells which interferes with various cellular processes. Given this background, the clinical diagnostic significance of bilirubin, in tests for liver and other related organ functions, is self evident.

Perhaps the most widely used assay for bilirubin has been the so called diazo method. In the diazo method, a sample suspected of containing bilirubin is contacted with a reagent composition which includes a diazonium salt. The diazonium salt reacts with bilirubin to form two azobilirubin fragments. The azobilirubin has an extinction coefficient which is higher than that of bilirubin itself and is easily detectable.

Many diazonium salts have been suggested for use in the diazo method for determining bilirubin. For example, in 1883 Ehrlich discovered that diazotized sulfanilic acid couples with bilirubin to give a yellow diazobilirubin pigment. Since then many other diazonium salts have been suggested. Certain 2,4- and 2,5-phenyldiazonium salts, for example 2,4- and 2,5-dichlorophenyldiazonium salts, have been used for the detection of bilirubin in serum and urine. However, methods using these diazonium salts are known to be relatively insensitive. Further, some of these diazonium salts, when dry, are explosively unstable, i.e., subject to shock induced decomposition.

One recently suggested diazonium salt for the determination of bilirubin is diazotized sulfanilamide. This diazonium salt gives a reddish-purple azobilirubin in an acidic environment. Unfortunately, this diazonium salt is less stable to shock than desired. This method is described in Chin-Chung Chen et al, "Sulfanilamide for the Determination of Total Bilirubin", *Clin Chem*, Vol. 26, No. 7, p. 990, 1980. Chen et al generated the sulfanilamide in situ in the reaction solution and therefore would not have been concerned with the shock sensitivity of the dry diazonium salt.

As noted, several of the previously proposed diazonium salts are explosively unstable when dry. This instability makes handling of these compounds, either during manufacture of reagent compositions or during use, hazardous. This is particularly true where the desired product is a dry reconstitutable reagent composition or dry analytical element. Handling large quantities of a potentially explosive material in a large scale packaging or coating process is undesirable. Thus, any reduction in explosion hazard is desirable.

It is readily apparent that there is a continuing need for new diazonium salts for use in the analysis of bilirubin. Desirably, new diazonium salts should be relatively shock stable in dry form. Further, the new diazonium salts should provide a sensitive and accurate assay for bilirubin.

SUMMARY OF THE INVENTION

We have found that certain substituted sulfanilamide and carbonamide diazonium salts are less prone to shock induced decomposition than are the unsubstituted sulfanilamide diazonium salts, yet still provide for accurate and sensitive bilirubin assays. The new diazonium salts according to the present invention have the structural formula:

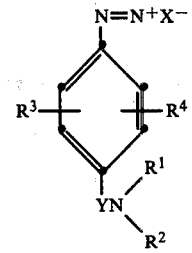

wherein $X^-$ is a stabilizing anion, Y is CO— or SO$_2$—; and $R^1$ and $R^2$ are independently selected from hydrogen, alkyl, aryl, carboxyalkyl and hydroxyalkyl providing $R^1$ and $R^2$ are not both hydrogen; $R^3$ and $R^4$ are independently selected from groups such that the sum of the Hammett sigma values for $R^3$ and $R^4$ does not exceed $+0.4$ or $R^3$ and $R^4$ represent the carbon atoms necessary to complete a carbocyclic fused ring structure.

In another embodiment of the present invention the diazonium salt described above is included in a dry reagent composition. Alternatively, the dry reagent composition comprises reagents which are capable of producing the described diazonium salt in situ. Thus, in accordance with another embodiment of the present invention there is provided an improved dry reagent composition comprising:

(a) an acid and (b) a diazonium salt or reagents capable of producing a diazonium salt when contacted with water, wherein the diazonium salt is as described above.

The reagent composition described above is particularly useful in a dry analytical element. Thus, in accordance with another embodiment of the present invention, there is provided a dry analytical element comprising a carrier matrix having therein the described reagent composition. In preferred embodiments the dry analytical element comprises a support having thereon a nonfibrous isotropically porous spreading layer. For reasons which will become apparent in the detailed description of the invention, it is desirable to have the reagent composition in the porous spreading layer. In still more preferred embodiments the dry analytical element comprises a support having thereon, in order:

(1) a layer comprising a hydrophilic binder and a buffer capable of buffering the layer to a pH of about 3.0 to 7.0, and (2) a nonfibrous isotropically porous spreading layer which is translucent when wet having therein the described reagent composition.

The diazonium salts of the present invention provide compositions, elements and methods which are extremely sensitive to bilirubin. The diazonium salts are less shock sensitive than comparable diazonium salts of the prior art and yet retain the ability to couple with bilirubin to produce azobilirubins. Certain of the diazonium salts of the present invention provide these advantages and in addition, are more sensitive to bilirubin than are previously known diazonium salts, particularly at high bilirubin concentrations.

DETAILED DESCRIPTION OF THE INVENTION

The diazonium salts of the present invention have the structural formula:

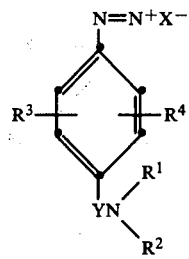

wherein $X^-$ is a stabilizing anion, Y is CO— or $SO_2$—; and $R^1$ and $R^2$ are independently selected from hydrogen, alkyl, preferably having from 1 to 20 carbon atoms such as methyl, isopropyl, dodecyl, aryl such as benzyl, and carboxyalkyl and hydroxyalkyl, preferably wherein the alkyl group is lower alkyl, i.e., having 1–4 carbon atoms such as carboxymethyl, carboxyethyl, hydroxymethyl, hydroxyethyl, tris(hydroxymethyl)methyl and hydroxybutyl; providing $R^1$ and $R^2$ are not both hydrogen; $R^3$ and $R^4$ are independently selected from groups which are electron donor groups or mildly electron withdrawing groups such that the sum of the Hammett sigma values for $R^3$ and $R^4$ does not exceed +0.4. Examples of these groups include hydrogen, halogen, e.g., chloro; bromo, lower alkyl, e.g., methyl, propyl; alkylthio, e.g., methylthio; lower alkoxy, e.g., methoxy, ethoxy; aralkoxy, e.g., benzyloxy; phenylthio; and alkylamino, e.g., acetamino or $R^3$ and $R^4$ represent the carbon atoms necessary to complete a fused carbocyclic ring structure such as naphthyl, indyl, or anthryl, including such ring structures substituted with the other groups identified for $R^3$ and $R^4$.

Stabilizing anions for diazonium salts are known. These anions make possible the isolation of the salts in dry form and provide for long term thermal stability as well as reduced shock sensitivity. Borofluoride salts of diazobenzene p-sulfonic acid are described in U.S. Pat. No. 3,511,607.

In the formula above, $X^-$ is preferably the anion of a Lewis acid coordinatively saturated by a hydrogen halide. Useful stabilizing anions include tetrafluoroborate, hexafluorophosphate, chlorozincate and hexafluorotitanate. The diazonium salts containing the above anions have been found to be more stable to long term keeping, particularly in a dry analytical element format, than are the diazonium salts which contain other anions. Of the preferred anions, hexafluorophosphate has been found to be particularly preferred since the long term keeping of the diazonium salts with this anion are still further improved over salts which contain other Lewis acid type anions. For example, the hexafluorophosphate salts are more stable than are the tetrafluoroborate salts in long term keeping in a dry analytical element. Other useful anions include arylsulfonates, such as naphthylene disulfonate and 4,4'-biphenyldisulfonate.

In a particularly preferred embodiment, Y is $SO_2$, $R^1$ is hydrogen and $R^2$ is carboxymethyl. These compounds form an azobilirubin which has an extremely high extinction coefficient. Further, in dry analytical elements, these compounds have been found to be more sensitive to high levels of bilirubin than a closely related compound, namely, the unsubstituted sulfanilamide. The currently preferred compound is 4-(N-carboxymethylsulfamyl)benzene diazonium hexafluorophosphate. Other useful compounds include the following:

4-[N,N-bis(carboxymethyl)sulfamyl]benzenediazonium hexafluorophosphate 4-(N,N-bishydroxyethylsulfamyl)benzenediazonium hexafluorophosphate 4-(N-carboxymethylcarbamyl)benzenediazonium tetrafluoroborate 4-(N-carboxypropylcarbamyl)benzenediazonium naphthylenedisulfonate 4-(N-carboxymethylsulfamyl)benzenediazonium tetrafluoroborate 4-(N-dodecylsulfamyl)benzenediazonium tetrafluoroborate 3,5-dichloro-4-(N-carboxymethylsulfamyl)benzenediazonium hexafluorophosphate 4-(N-carboxymethylsulfamyl)-1-diazonium naphthylene hexafluorophosphate 7-[N-tris(hydroxymethyl)methylcarbamyl]-4-diazoniumindene hexafluorophosphate 4-[N,N-bis(carboxymethyl)sulfamyl]-1-diazonium-6-methoxy naphthylene chlorozincate Compounds according to the present invention are made by methods which are well known in the art. To illustrate, the preferred sulfonamide compounds are made by first reacting an acetanilide with chlorosulfonic acid to produce N-acetylsulfanilyl chloride. This sulfonyl chloride is then reacted with an amine such as glycine and the N-acetyl group is removed by acid hydrolysis to produce the desired sulfonamide. The sulfonamide is then diazotized using sodium nitrite and an acid such as hydrochloric acid to produce the desired diazonium salt. The desired anion for the diazonium salt is provided by including a salt of the anion in the diazotization reaction mixture. For example, if sodium hexafluorophosphate is included in this reaction mixture, the hexafluorophosphate diazonium salt is produced.

An acid pH is desirable to improve the storage stability of the diazonium salt and promote the coupling with bilirubin. Thus, reagent compositions within the scope of the present invention include the diazonium salt as described and an acid. Where the reagent composition is in the form of an aqueous solution, any acid is useful, such as mineral acids, for example, hydrochloric acid sulfuric acids. Where a dry reagent composition is desired, it is preferred to use acids which are solid when anhydrous. Useful acids of this type include malic, sulfosalicylic, tartaric, succinic, cyclohexanesulfamic, p-toluenesulfonic and citric. Where it is desirable to include the reagent composition in a carrier, it is desirable to provide an acid which does not degrade the carrier matrix or to provide a combination of reagents which are capable of generating the acid in situ on contact with water. Useful acids of this type include a solid adduct of a Friedel Crafts salt and an organic Lewis base with a weak acid such as an organic acid as described in U.S. Pat. No. 3,814,586. Upon contact with water, such a mixture provides a sufficiently acidic environment to promote the coupling of the diazonium salt with bilirubin.

The amount of acid used varies widely. In preferred embodiments, the amount of acid is sufficient to provide a pH between about 3 and 7 under conditions of use.

In some embodiments of the present invention the reagent composition is included in a spreading layer of a dry analytical element. Some spreading layers, for example the barium sulfate spreading layers described more completely below, are capable of providing an environment which is sufficiently acidic without the need for an additional acid. In these embodiments, the spreading layer components are considered to be the acid of the reagent composition.

In preferred embodiments the reagent composition of the present invention includes what is known in the art as a "diazo bilirubin promoter" sometimes also referred to as an "accelerating agent". These promoters are compounds which are known to promote the rate of diazobilirubin formation. Useful agents include dyphylline, caffeine, sodium acetate, sodium benzoate and gum arabic. The currently preferred diazobilirubin promoter is dyphylline since dyphylline produces a reagent composition with excellent long term keeping characteristics.

The reagent composition is prepared in a variety of forms. For example, the reagent optionally is prepared as a lyophilyzed powder or tablets which are reconstituted with water to produce a reagent solution. Techniques for making such forms of reagent compositions and materials such as fillers, binders and the like are well known in the art.

The diazonium salts of the present invention are useful in conventional solution assays and in dry analytical elements. A solution assay is carried out by adding a sample to a solution containing the diazonium salt. The presence of bilirubin in the sample is indicated by a change in color of the solution which is measured visually or by means of an instrument such as a spectrophotometer. Where a dry analytical element is desired, the reagent composition of the invention is coated on a suitable support and the resulting layer is dried. Contact of the element with a sample dissolves the reagent and again the presence of bilirubin in the sample is indicated by a change in the color of the reagent layer.

In its simplest form, dry analytical elements of the present invention comprise a carrier matrix impregnated with the described reagent composition. Useful carrier matrixes are insoluble and maintain their structural integrity when exposed to water or physiological fluids such as serum or urine. Useful carrier matrixes include paper, cellulose, wood, glass fiber, woven and nonwoven fabrics. A useful dry analytical element is made by imbibing a solution containing the reagent composition in the matrix and drying. Useful materials and elements which are adapted to use the described reagent composition are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,993,594, 3,936,357, 4,270,920, 4,248,829, 4,255,384, 4,256,693, and U.K. Pat. No. 2,052,057.

In preferred dry analytical elements the element comprises a support having thereon a non-fibrous isotropically porous spreading layer. The spreading layer has therein the described reagent composition. It is desirable to include the reagent composition in such a porous spreading layer, as opposed to a hydrophilic binder layer, since bilirubin is frequently bound to relatively large proteins and the porous layer provides for contact between the bound bilirubin and the reagent composition. Further, many diazonium salts are less stable than desired in hydrophilic binders such as gelatin. Useful isotropically porous spreading layers are disclosed in U.S. Pat. No. 3,992,158. In one embodiment, particulate materials are used to form the layers and isotropic porosity is created by interconnected spaces between the particles. Alternatively, such layers are prepared using isotropically porous polymers, for example, "blush" polymers.

A preferred isotropically porous spreading layer contains particulate materials such as titanium dioxide. Microcrystalline cellulose, which is commercially available from FMC Corporation under the name Avicel ®, is another example of a material which is preferred for use in the present invention. A particularly preferred material is barium sulfate.

Another useful isotropically porous spreading layer is the bead spreading layer described in U.S. Pat. No. 4,258,001. The bead spreading layers of this patent contain polymer particles held together by a small amount of adhesive located between adjacent particles where the particles are in closest proximity.

As noted above, bilirubin is frequently bound to a larger protein molecule such as albumin. Further, the azobilirubin molecule itself is relatively large. As a result, the azobilirubin that is generated in the layer containing the reagent composition is usually distributed throughout the layer rather than being concentrated at either the bottom or the top of the layer. Thus, in order to measure substantially all of the azobilirubin that is generated, it is desirable that the spreading layer be translucent when wet. In a translucent spreading layer, whether observed visually or by means of a spectrophotometer, all of the azobilirubin which is produced, even that which is deep within the layer, is detectable. Useful translucent when wet spreading layers include the layers containing Avicel ®, barium sulfate and the bead spreading layer of U.S. Pat. No. 4,258,001. These layers, when contacted with serum are translucent.

In particularly preferred embodiments, the dry analytical element of the present invention includes a hydrophilic layer between the support and the spreading layer which contains the reagent composition. While the reasons are not clearly understood, such a hydrophilic layer between the support and reagent composition layer improves the observed response of the element, particularly to high levels of bilirubin. Further, the hydrophilic layer reduces the difference in spreading characteristics between samples which have high and low protein content. It is desirable to include in the hydrophilic layer a buffer which is capable of maintaining a pH of about 3.0–7.0 under conditions of storage. Such a buffered hydrophilic layer has been found to improve the long term keeping of the dry analytical element. Useful buffers include partially neutralized acids such as partially neutralized 3,3-dimethylglutaric acid (buffer to pH 6), and malic acid (buffer to pH 5). The binder for the hydrophilic layer is any of a wide variety of hydrophilic film-forming materials, such as gelatin or agarose. Gelatin is the preferred hydrophilic material. In preferred embodiments, the gelatin is crosslinked by well known crosslinking agents to provide structural integrity under conditions of manufacture and use.

To use the dry analytical elements of the present invention, the elements are contacted with a liquid sample. Any bilirubin in the sample reacts with the diazonium salt to produce a diazobilirubin pigment that generally has a maximum absorption at a wavelength between 500 and 540 nm. The diazobilirubin pigment is detected either visually or by means of a spectrophotometer after any bilirubin in the sample has had a change to react. It was found that the bilirubin within the sample would react quickly with the diazonium salt. However, after about one to two minutes, the apparent optical density produced by the diazobilirubin pigment very gradually decreases. While such an element is certainly useful in assaying for bilirubin, some care must be taken to make all measurements at approximately the same time after contact with the sample. In order to reduce this problem, it was found that by placing a small amount of a cationic mordant in the hydrophilic layer, the decrease in apparent density over time was substantially eliminated. Useful cationic mordants are disclosed in U.S. Pat. No. 4,069,017. The currently preferred mordant is poly(styrene-co-N-vinylbenzyl-N,N-dimethylbenzylammonium chloride-co-divinylbenzene).

In practicing the method according to the present invention, the sample is contacted with a reagent composition, either in solution or in dry form. Any azobilirubin which is produced is detected either visually or spectrophotometrically. While the exact wavelength of maximum absorption depends upon the diazonium salt which is chosen, generally, the salts of the present invention produce azobilirubin pigments which absorb between 500 and 540 nm. The reaction of the salts of the present invention with bilirubin is extremely rapid. Thus, the amount of azobilirubin which is produced is measured within minutes after contacting the sample with the reagent composition.

The following examples are presented to illustrate the invention.

EXAMPLE 1

4-(N-carboxymethylsulfamyl)benzenediazonium hexafluorophosphate was made by reacting N-acetylsulfanilyl chloride with glycine, preparing the hydrochloride of the product and then diazotizing.

4-(N-carboxymethylsulfamyl)acetanilide 35 g of glycine were dissolved in 250 mL water with 80 g of 50 percent sodium hydroxide solution. 120 g of N-acetylsulfanilyl chloride were added with vigorous stirring. The stirring was continued for 2 hours, whereupon the mixture was filtered to remove a small amount of insoluble material. The clear filtrate was acidified with hydrochloric acid and the precipitated product was filtered off and washed with water.

4-(N-carboxymethylsulfamyl)aniline.HCl 80 g of 4-(N-carboxymethylsulfamyl)acetanilide were heated under reflux for 40 minutes with a solution of 100 mL concentrated hydrochloric acid diluted to 250 mL with water. The resulting clear solution was chilled and the aminehydrochloride was filtered and washed with acetone.

4-(N-carboxymethylsulfamyl)benzenediazonium hexafluorophosphate 27 g of 4-N-carboxymethylsulfamyl aniline hydrochloride were dissolved in 200 mL cold water. Ice was added to make a total volume of 400 mL. 25 mL concentrated hydrochloric acid were added with stirring, followed by the addition of a solution of 8 g sodium nitrite in 40 mL of water. The reaction mixture was filtered to remove any insoluble material and then 29 mL of 65 percent hexafluorophosphoric acid were added with stirring. The mixture was chilled in an ice-/alcohol bath and the diazonium salt was filtered off and washed with cold water.

EXAMPLES 2-4

Dry analytical elements containing a variety of diazonium salts were prepared. Represented schematically, the elements had the structure:

Spreading layer containing the reagent composition:
  diazonium salt, barium sulfate, cellulose acetate binder, polyurethane, Triton X ®-100
Subbing layer: poly(N-isopropylacrylamide)
Hydrophilic mordant-buffer layer: gelatin, mordant, malic acid, Surfactant 10G ®, gelatin hardener
Support: poly(ethylene terephthalate)

The polyurethane binder in the spreading layer promotes the cohesion of the spreading layer and is available from the B. F. Goodrich Co. under the name Estane ®. The mordant in the mordant-buffer layer is poly(styrene-co-N-vinylbenzyl-N,N-dimethylammonium chloride-co-divinylbenzene). The barium sulfate functions as both the particulate material in the spreading layer as well as the acid for the reagent composition. The subbing layer is present to promote the adhesion of the spreading layer.

Two samples of each element were spotted with 10 μL bilirubin calibrator solutions. One sample was spotted with a solution containing 10.4 mg/dL of bilirubin and the second sample with a solution containing 24.3 mg/dL of bilirubin. Using a spectrophotometer, the reflectance density was monitored through the support of the element for a period of time after spotting. For each element a $\Delta D_R$ was calculated which was the difference between the reflectance density produced by the high bilirubin level calibrator minus the density produced by the low level calibrator. The results are indicated in Table 1.

TABLE 1

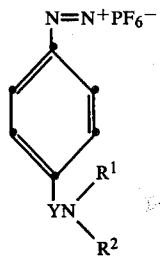

| Example | Y | R¹ | R² | $\Delta D_R$ |
|---|---|---|---|---|
| 2 | $SO_2-$ | $-H$ | $-CH_2COOH$ | 0.183 |
| 3 | $SO_2-$ | $-CH_2COOH$ | $-CH_2COOH$ | 0.136 |
| 4 | $SO_2-$ | $-CH_2CH_2OH$ | $-CH_2CH_2OH$ | 0.132 |

The fact that each diazonium salt produced a positive and significant $\Delta D_R$ in this test indicates that each is useful in a bilirubin assay.

EXAMPLE 5

This example includes a comparison with a previously known diazonium salt for a bilirubin assay.

To elements were prepared in a manner similar to Examples 2-4 except that the spreading layers also contained the diazobilirubin promoter dyphylline.

Samples of the elements were tested as in Examples 2-4 and the results are indicated in Table 2.

TABLE 2

| Example | Y | R¹ | R² | $\Delta D_R$ |
|---|---|---|---|---|
| 5 | $SO_2-$ | $-H$ | $-CH_2COOH$ | 0.242 |
| Comparison | $SO_2-$ | $-H$ | $-H$ | 0.179 |

The data from Table 2 show that the preferred diazonium salt of the present invention produces about 35 percent more signal than does the known unsubstituted p-sulfonamido benzene diazonium salt. Further, a comparison of the $\Delta D_R$ for the element of Example 5 (0.242) with the $\Delta D_R$ for that of Example 2 (0.183) illustrates the improvement obtained with the dyphylline promoter.

EXAMPLE 6

An element was prepared which was similar to that of Example 5 except that the diazonium salt was 4-(N-carboxymethylcarbamyl)benzenediazonium tetrafluoroborate. The element was tested in a manner similar to elements of Examples 2-4 except that the calibrator solutions contained 9.7 mg/dL and 23.6 mg/dL of bilirubin, respectively. The $\Delta D_R$ for this element was 0.184 indicating that this diazonium salt provides a useful bilirubin assay.

EXAMPLE 7

An element was prepared which was similar to the element of Example 5 except that the spreading layer contained titanium dioxide as the particulate material. The layer also contained 0.14 g/m² of 5-sulfosalicylic acid. Thus, while the spreading layer of Example 5 was translucent when wet, the spreading layer of this example was opaque. The results of testing were as follows:

| Example 5 translucent spreading layer | $\Delta D_R = 0.242$ |
|---|---|
| Example 7 opaque spreading layer | $\Delta D_R = 0.190$. |

This result illustrates the improved results which are obtained from elements having a translucent spreading layer.

EXAMPLE 8

This example illustrates the reduced shock sensitivity of the compounds of the present invention in comparison to diazotized sulfanilamide.

The shock sensitivity is determined in a drop weight impact tester. In this test 40 mg of the compound to be tested is placed in a brass cup. A close fitting piston is placed in the cup on top of the compound. A weight is dropped onto the piston from various heights and, for each test, the energy received by the sample is recorded as the change in potential energy of the dropped weight in joules. In addition, means for measuring the amount of gases given off by a decomposing sample, if any, is provided. Each compound is subjected to about 20 tests and the statistically determined number given a compound is the potential energy (in joules) which would result in decomposition (shockrelated to both the ease of SID and the amount of gas given off. Thus, for example, a compound which requires only 10 joules is more hazardous than one which requires 20 joules. Similarly a compound which gives off little or no gas is less hazardous than one which gives off 1 or more cc of gas per 40 mg of sample. The result of testing a series of compounds is given in Table 3.

TABLE 3

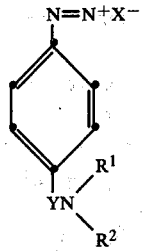

| | Y | X⁻ | R1 | R2 | SID | Gas |
|---|---|---|---|---|---|---|
| Comparative | $SO_2-$ | $PF_6$ | $-H$ | $-H$ | 15 | up to 1.77 cc |
| Cpd A | $SO_2-$ | $PF_6$ | $-CH_2CH_2OH$ | $-CH_2CH_2OH$ | 42 | none |
| Cpd B | $SO_2-$ | $PF_6$ | $-H$ | $-CH_2COOH$ | 43 | none |
| Cpd C | $SO_2-$ | $PF_6$ | $-CH_2COOH$ | $-CH_2COOH$ | 25 | none |

TABLE 3-continued

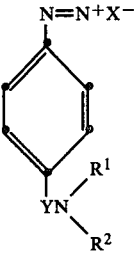

| | Y | X⁻ | R1 | R2 | SID | Gas |
|---|---|---|---|---|---|---|
| Cpd D | CO— | BF$_4$ | —H | —CH$_2$COOH | >62 | no SID |

These results show that the compounds of the present invention are less subject to shock induced decomposition than is a comparable known compound. As a further comparison the most commonly used diazonium salt for bilirubin determination (diazotized sulfanilic acid) has a SID at about 6.8 joules.

The invention has been described in detail with particular reference to preferred embodiments thereof, but it will be understood that variations and modifications can be effected within the spirit and scope of the invention.

What is claimed is:

1. A compound of the formula:

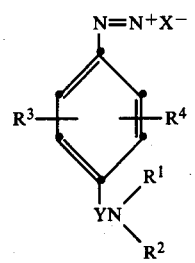

wherein X⁻ is a stabilizing anion, Y is CO— or SO$_2$—; and R$^1$ and R$^2$ are independently selected from hydrogen, alkyl, aryl, carboxyalkyl and hydroxyalkyl providing R$^1$ and R$^2$ are not both hydrogen; R$^3$ and R$^4$ are independently selected from groups such that the sum of the Hammett sigma values for R$^3$ and R$^4$ does not exceed +0.4 or R$^3$ and R$^4$ represent the carbon atoms necessary to complete a fused carbocyclic ring structure.

2. A reagent composition comprising an acid and a diazonium salt or reagents capable of producing a diazonium salt when contacted with water wherein said diazonium salt is represented by the formula:

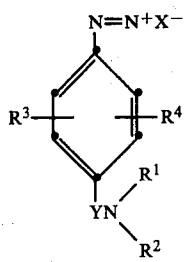

wherein X⁻ is a stabilizing anion, Y is CO— or SO$_2$—; and R$^1$ and R$^2$ are independently selected from hydrogen, alkyl, aryl, carboxyalkyl and hydroxyalkyl providing R$^1$ and R$^2$ are not both hydrogen; R$^3$ and R$^4$ are independently selected from groups such that the sum of the Hammett sigma values for R$^3$ and R$^4$ does not exceed +0.4 or R$^3$ and R$^4$ represent the carbon atoms necessary to complete a fused carboxylic ring structure.

3. The reagent composition according to claim 2 comprising a diazobilirubin accelerating agent.

4. A dry analytical element comprising a carrier matrix having therein a reagent composition comprising an acid and a diazonium salt or reagents capable of producing a diazonium salt when contacted with water wherein said diazonium salt has the structural formula:

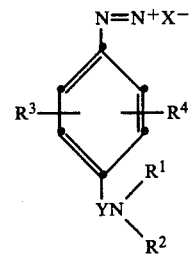

wherein X⁻ is a stabilizing anion, Y is CO— or SO$_2$—; and R$^1$ and R$^2$ are independently selected from hydrogen, alkyl, aryl, carboxyalkyl and hydroxyalkyl providing R$^1$ and R$^2$ are not both hydrogen; R$^3$ and R$^4$ are independently selected from groups such that the sum of the Hammett sigma values for R$^3$ and R$^4$ does not exceed +0.4 or R$^3$ and R$^4$ represent the carbon atoms necessary to complete a fused carbocyclic ring structure.

5. The dry analytical element according to claim 4 comprising a diazobilirubin promoter.

6. A dry analytical element comprising a support having thereon a nonfibrous isotropically porous spreading layer having therein a reagent composition comprising an acid and a diazonium salt or reagents capable of producing a diazonium salt when contacted with water wherein said diazonium salt is represented by the formula:

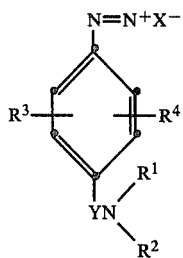

wherein $X^-$ is a stabilizing anion, Y is CO— or $SO_2$—; and $R^1$ and $R^2$ are independently selected from hydrogen, alkyl, aryl, carboxyalkyl and hydroxyalkyl providing $R^1$ and $R^2$ are not both hydrogen; $R^3$ and $R^4$ are independently selected from groups such that the sum of the Hammett sigma values of $R^3$ and $R^4$ does not exceed +0.4 or $R^3$ and $R^4$ represent the carbon atoms necessary to complete a fused carbocyclic ring structure.

7. The dry analytical element according to claim 6 comprising a diazobilirubin promoter.

8. The dry analytical element according to claim 6 wherein said spreading layer is translucent when wet.

9. A dry analytical element comprising a support having thereon, in order:
   (1) a layer comprising a hydrophilic binder and a buffer capable of buffering the layer to a pH of about 3.0–7.0,
   (2) a nonfibrous isotropically porous spreading layer which is translucent when wet having therein
      (a) an acid,
      (b) a diazobilirubin promoter and,
      (c) a diazonium salt or reagents capable of producing a diazonium salt when contacted with water wherein said diazonium salt is represented by the formula:

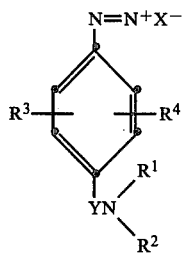

wherein $X^-$ is a stabilizing anion, Y is CO— or $SO_2$—; and $R^1$ and $R^2$ are independently selected from hydrogen, alkyl, aryl, carboxyalkyl and hydroxyalkyl providing $R^1$ and $R^2$ are not both hydrogen; $R^3$ and $R^4$ are independently selected from groups such that the sum of the Hammett sigma values for $R^3$ and $R^4$ does not exceed +0.4 or $R^3$ and $R^4$ represent the carbon atoms necessary to complete a fused carbocyclic ring structure.

10. The dry analytical element according to claim 9 wherein layer (1) comprises a cationic mordant.

11. In a method for the quantitation of bilirubin in a sample said method comprising the steps of
   (1) contacting said sample with a reagent composition comprising an acid and a diazonium salt and
   (2) measuring the amount of azobilirubin formed
the improvement wherein said diazonium salt has the formula:

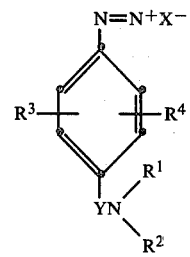

wherein $X^-$ is a stabilizing anion, Y is CO— or $SO_2$—; and $R^1$ and $R^2$ are independently selected from hydrogen, alkyl, aryl, carboxyalkyl and hydroxyalkyl providing $R^1$ and $R^2$ are not both hydrogen; $R^3$ and $R^4$ are independently selected from groups such that the sum of the Hammett sigma values for $R^3$ and $R^4$ does not exceed +0.4 or $R^3$ and $R^4$ represent the carbon atoms necessary to complete a fused carbocyclic ring structure.

12. The invention according to claim 1, 2, 4, 6, 9 or 11 wherein Y is $SO_2$—.

13. The invention according to claim 1, 2, 4, 6, 9 or 11 wherein $X^-$ is the anion of a Lewis acid coordinatively saturated by a hydrogen halide.

14. The invention according to claim 1, 2, 4, 6, 9 or 11 wherein said anion is hexafluorophosphate.

15. The invention according to claim 1, 2, 4, 6, 9 or 11 wherein $R^1$ is hydrogen and $R^2$ is carboxymethyl.

16. The invention according to claim 2, 4, 6, 9 or 11 wherein said diazonium salt is 4-(N-carboxymethylsulfamyl)benzenediazonium hexafluorophosphate.

17. 4-(N-carboxymethylsulfamyl)benzenediazonium hexafluorophosphate.

* * * * *